United States Patent [19]

Clark

[11] 4,286,815

[45] Sep. 1, 1981

[54] LENS INSERTION AND REMOVAL DEVICE

[75] Inventor: James A. Clark, Honeoye Falls, N.Y.

[73] Assignee: Bausch & Lomb Incorporated, Rochester, N.Y.

[21] Appl. No.: 108,209

[22] Filed: Dec. 28, 1979

Related U.S. Application Data

[63] Continuation-in-part of Ser. No. 915,842, Jun. 15, 1978, abandoned.

[51] Int. Cl.$^3$ .............................................. A61F 9/00
[52] U.S. Cl. ............................... 294/1 CA; 294/64 R
[58] Field of Search ............... 294/1 CA, 64 R, 64 A, 294/64 B; 128/303 R; 206/5.1; 271/90, 97, 98, 106; 351/160

[56] References Cited

U.S. PATENT DOCUMENTS

| | | | |
|---|---|---|---|
| 1,495,881 | 5/1924 | Bunger | 294/64 R |
| 1,737,401 | 11/1929 | Atzert | 294/64 R |
| 2,967,731 | 1/1961 | Swartz | 294/64 R |
| 3,177,874 | 4/1965 | Spriggs | 294/1 CA X |
| 3,424,486 | 1/1969 | Corley | 294/64 R |
| 3,879,076 | 4/1975 | Barnett | 294/1 CA |
| 4,026,591 | 5/1977 | Cleaveland | 294/1 CA |
| 4,047,532 | 9/1977 | Phillips et al. | 294/64 R X |
| 4,123,098 | 10/1978 | Shoup | 294/64 R X |

OTHER PUBLICATIONS

*Vacuum Pen*, Research Disclosure by Kodak Ltd. and J. S. Eeles, No. 128, p. 46.

*Primary Examiner*—Johnny D. Cherry
*Attorney, Agent, or Firm*—Frank C. Parker; John S. Norton

[57] ABSTRACT

A device for facilitating the insertion and removal of a soft contact lens from a human eye, including a suction cup, a tunnel extension on one side of the suction cup, a vacuum source for applying vacuum through the suction cup to the lens and a collapsible member between the cup and the vacuum source. Upon placement of the suction cup over the lens such that the tunnel extension extends over the edge of the lens, the edge of the lens under the tunnel is caused to lift from the eye when vacuum is applied thereto and the suction created draws the entire lens against the suction cup. The collapsible member between the vacuum source and the suction cup collapses causing the suction cup holding the contact lens to move automatically away from the eye.

7 Claims, 5 Drawing Figures

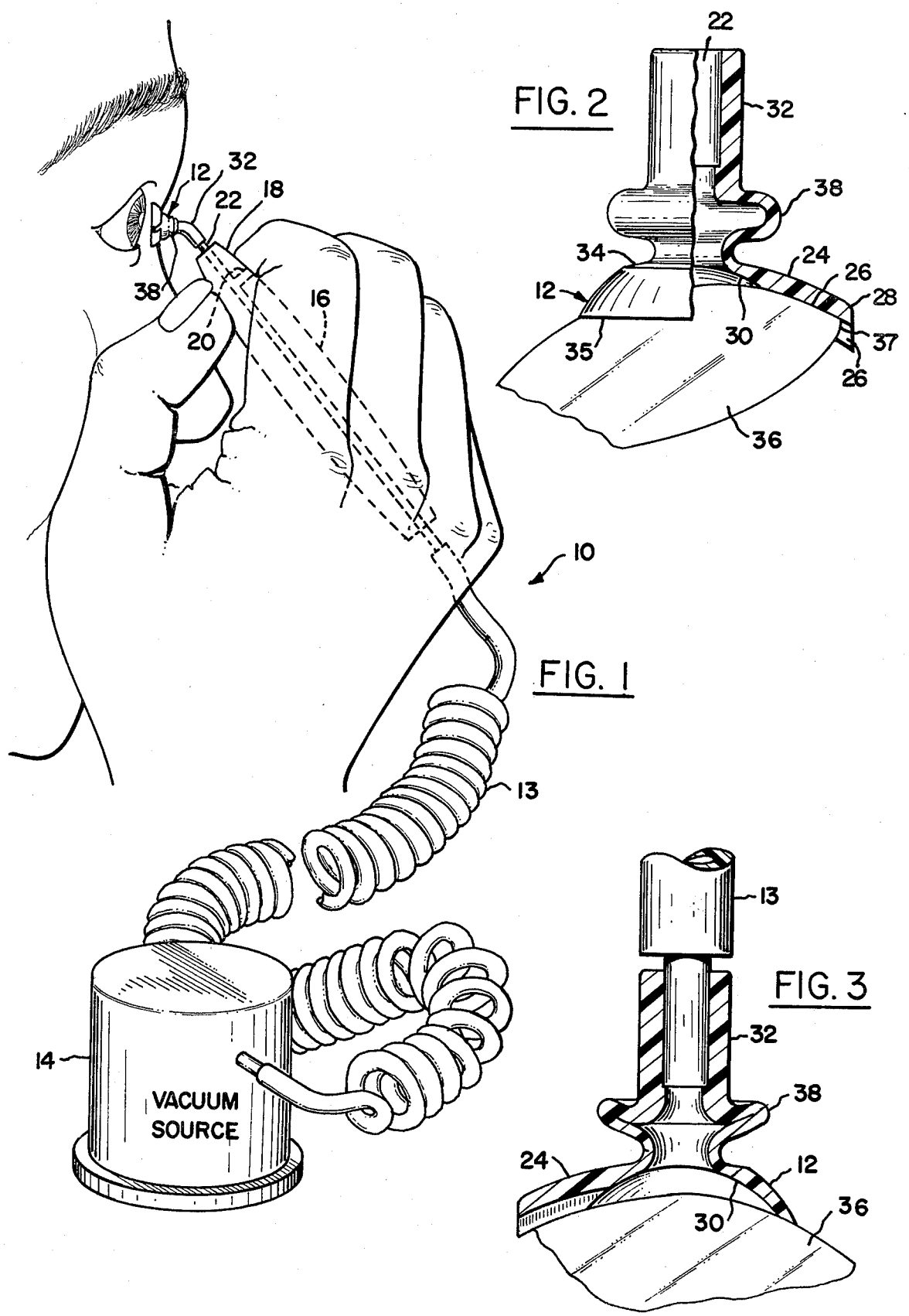

TO VACUUM
SOURCE 14

LENS INSERTION AND REMOVAL DEVICE

CROSS-REFERENCE TO RELATED APPLICATIONS

This application is a continuation-in-part of Ser. No. 915,842, filed June 15, 1978, for James A. Clark, entitled "Lens Insertion Device", and now abandoned.

BACKGROUND OF THE INVENTION

In recent years dramatic improvements in the contact lens art have resulted in widespread use of contact lenses and particularly, soft contact lenses. One of the recurring difficulties in the use of such lenses, however, has been the insertion and removal of the lens from the eye by both practitioners when fitting the lens and by the wearer during everyday use. Numerous attempts to overcome these difficulties in the past through the use of various mechanical devices have been suggested, but such devices have met with varying degrees of success. Examples of such devices are disclosed in the following listed patents:

| PATENT No. | TITLE | INVENTORS |
|---|---|---|
| 2,379,629 | Device for Manipulating Contact Lenses | Eric W. Eweson |
| 2,384,334 | Pneumatic Pickup Device | Frank G. Olson |
| 2,919,696 | Instrument for Applying Contact Lenses | August Rinaldy |
| 3,031,918 | Instrument for Contact Lens Placement | Charles R. Moyers |
| 3,091,328 | Contact Lens Remover and Carrier | Priscilla A. Leonardos |
| 3,129,971 | Contact Lens Applicator | Arnold J. Kobler |
| 3,132,887 | Applicator for Contact Lenses | Miguel Martinez |
| 3,139,928 | Instrument for Inserting Corneal Lenses | Richard H. Grabiel |
| 3,177,874 | Contact Lens Applicator | John D. Spriggs |
| 3,298,502 | Double End Contact Lens Holder and Moistener | Gilbert Schwartzman |
| 3,304,113 | Instrument for Manipulating Contact Lenses | William R. Hutchison |
| 3,344,461 | Contact Lens Handling Apparatus | Dennis W. Floor |
| 3,411,364 | Contact Lens Instrument | Donald W. Horley & Donald R. Korb |
| 3,424,486 | Contact Lens Handling Apparatus | Clifton Corley |
| 3,490,806 | Contact Lens Digital Applicator | Ana Lopez-Calleja & Luis P. Saenz |
| 3,584,908 | Contact Lens Holder | Frank Ray |
| 3,600,028 | Device for Inserting and Removing Contact Lenses | Wilhelm Henning |
| 3,608,946 | Device for Handling of a Filter Membrane | Edward D. Erickson & Robert L. Wilson |
| 3,645,576 | Eye Contact Lens Manipulator | Eugene S. Horres |
| 3,647,380 | Contact Lens Holder | Robert E. Middleton |
| 3,656,794 | Vacuum Cup Lifter for Shell Eggs | Robert C. McCord |
| 3,697,109 | Contact Lens Inserter | Ottis L. Parrent |
| 3,743,337 | Contact Lens Inserter | Ely J. Crary |
| 3,781,050 | Eye Contact Lens Manipulator | Eugene S. Horres |
| 3,791,689 | Contact Lens Holder | Roger S. Boone & Frank Pyot |
| 3,879,076 | Method and Apparatus for Applying and Removing a Soft Contact Lens | Robert O. Barnett |
| 3,897,968 | Aspirator-Type Contact Lens Fitting Aid | Robert E. Allen, Jr. |
| 3,910,618 | Contact Lens Applicator | Enrico Massenz |
| 3,912,317 | Vacuum Suction Type Manipulator | Makoto Ohnaka |
| 3,922,025 | Method and Apparatus for Applying and Removing Contact Lenses | Edward R. Updegraff |
| 3,934,914 | Device for Inserting and Removing Contact Lens | Eben H. Carruthers |
| 3,934,916 | Vacuum Pickup Cap | Thomas R. Baker |
| 3,940,172 | Vacuum-Actuated Pickup Instrument | Clifford L. Hutson & Leonidas C. Miller |
| 4,026,591 | Contact Lens Handling Tools | John A. Cleaveland |
| 4,037,866 | Contact Lens Applicator | Edward E. Price |
| 4,047,532 | Vacuum Forcep and Method of Using Same | Jack L. Phillips & Timothy E. Dickinson |
| 4,123,098 | Contact Lens Insertion & Retraction Device | Lee E. Sharp |

Nevertheless, a significant problem in relation to such devices remains in gently removing a lens from the eye without causing physical injury to the eye or damage to the contact lens. In particular, the aforementioned apparati fail to solve the problem of breaking the surface tension and suction created between the soft contact lens and the eye without tearing the lens from the eye.

Accordingly, it is an object of the present invention to provide an improved contact lens insertion and removal device which facilitates the insertion and removal of soft contact lenses from the eye, while at the same time:
- prevents contact between the contact lens and the fingers, fingernails or hands of the user;
- releases the normal vacuum created between the eye and a soft contact lens in use;
- provides protection for the eye against excessive pressure and force;
- provides both for removal and insertion of the lens; and
- is inexpensive and simple to manufacture.

SUMMARY OF THE INVENTION

The present invention is an improved device for inserting and removing contact lenses, particularly soft contact lenses, from the eye. The invention includes a suction cup, a tunnel extension projecting from the suction cup, a vacuum source connected to the suction cup and a collapsible member between the vacuum source and the cup. The extension includes a tunnel, or air passage, integrally formed therein. The suction cup and extension are similar in shape to an Eskimo igloo and entrance tunnel, but curved on the bottom to approximate the curvature of the eye. When the suction cup is placed against a contact lens on the eye, the tunnel extension lies across the edge of the lens and extends onto the sclera of the eye. When the device is placed against the contact lens positioned on the eye and vacuum is applied, air passes through the tunnel into the suction cup, lifting the edge of the lens from the eye thereby breaking the adhesion between the eye and the lens. The entire lens is then drawn against and seals the suction cup. The collapsible member collapses because of the vacuum created and the lens is automatically withdrawn from the eye.

In one preferred embodiment the invention may include a tubular handle interposed between the collapsible member and the vacuum source for conveying vacuum from the source to the suction cup. The handle may also provide means for gripping the device. The handle may further include a vacuum control for selectively supplying vacuum to the suction cup. The vacuum control in this embodiment is a vent which diverts the vacuum, thereby limiting the amount of the vacuum at the suction cup. The tubular handle may be constructed from solid material or flexible plastic tubing.

In one embodiment the tubular handle includes an angular connector or fitting for connecting the suction cup to the tubular handle. An additional fitting may be used to connect the handle to a flexible hose which itself is connected to the vacuum source. In an alternative embodiment the vacuum source may be directly connected to the tubular handle and held in the hand. In either of these embodiments, the vacuum is conveyed from the vacuum source to the suction cup. The fitting is angularly disposed on the tubular handle in order to permit gripping of the device as closely as possible to the eye, thereby facilitating precision in inserting and removing a lens from the eye, to prevent occluded viewing by the patient while inserting or removing a lens, and to allow the patient to use a mirror during insertion or removal. In an alternative embodiment, the tubular handle itself may be curved proximate to the suction cup in order to permit gripping of the device as closely as possible to the eye.

In order to remove a contact lens from the eye, the tubular handle is gripped and a finger is placed over the vacuum control causing air to flow in through the suction cup. The suction cup is then moved towards the eye and placed on the contact lens already in position on the eye, so that the tunnel extension is over the edge of the lens. Air passes at high velocity through the tunnel extending from the suction cup. This passage of air, as taught by the Bernoulli principle, causes low air pressure over the edge of the lens (under the tunnel) because of the high velocity of the air passing therethrough. In addition, air is forced under the edge of the lens. As a result, the edge of the lens under the tunnel is raised from the eye, sealing off the tunnel and breaking the suction between the underside of the lens and the eye. Thereafter, the remainder of the lens is caused to be drawn against the rim of the suction cup by the vacuum being supplied to it. When the lens is drawn against the rim of the suction cup which effectively seals the cup to the lens, the atmospheric pressure outside the aforementioned annular corrugation is greater than the air pressure within. This causes the corrugation to collapse, thereby drawing the lens away from the eye. After the handle is moved away from the eye, the lens may be placed in an appropriate receptacle.

In order to insert the lens in the eye, vacuum is used to fix the lens on the suction cup. Once the lens is on the suction cup the vacuum is released and the lens is held on the suction cup by means of the surface tension created between the lens and the cup. When the lens is placed on the eye, the surface tension created through interaction with the lacrymal fluid of the eye and the lens creates a greater surface tension between the lens and the eye than between the suction cup and the lens, thereby drawing the lens away from the suction cup as the tubular handle is removed from the proximity of the eye. Thus, by use of the present invention, contact lenses may be easily and safely inserted or removed from the eye without the use of fingers.

BRIEF DESCRIPTION OF THE DRAWINGS

FIG. 1 of the drawings is a side view showing an improved lens insertion device being used to remove a contact lens from the eye of the user.

FIG. 2 of the drawings is a partial section view of an improved lens insertion device.

FIG. 3 of the drawings is a partial plan view of an improved lens insertion device, showing in particular, the device automatically withdrawing the lens from the eye upon capture of the lens by the suction cup.

DETAILED DESCRIPTION OF THE PREFERRED EMBODIMENTS

Figure 4:
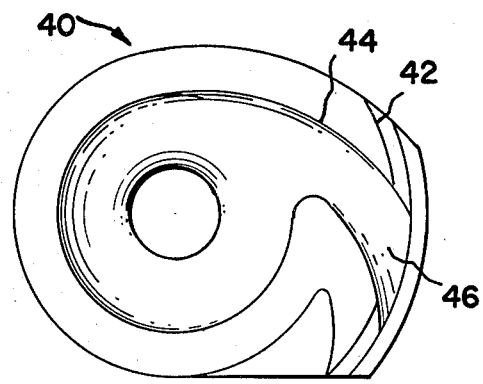
FIG. 4 of the drawings is a bottom view of one embodiment of the suction cup for an improved contact lens insertion and removal device.

While the invention is susceptible of embodiment in many different forms, there is shown in the drawings and will herein be described in detail, several specific embodiments, with the understanding that the present disclosure is to be considered as an exemplification of the principles of the invention and is not intended to limit the invention to the embodiments illustrated.

Improved contact lens insertion and removal device 10, as shown in FIG. 1, comprises a suction cup 12, connected by hose 13 to vacuum source 14. A tubular handle 16 is interposed between suction cup 12 and vacuum source 14. Tubular handle 16 is shaped so that gripping portion 18 is as close as possible to suction cup 12, in order to provide the greatest degree of precision in placement of the suction cup 12 on a contact lens. Tubular handle 16 includes vacuum control 20 for selectively supplying vacuum to suction cup 12. Additionally shown in FIG. 1 is connector 22 which connects suction cup 12 to tubular handle 16 and, as shown, forms an angle greater than 90° therebetween. Connector 22, in the preferred embodiment, is a hollow tube which conveys vacuum from vacuum source 14 to suction cup 12. The angular displacement allows the user to naturally and comfortably position his hand with respect to his eye, thereby allowing the greatest prevision in positioning suction cup 12 on a contact lens 36 which is in place on the eye.

As shown in FIG. 2 of the drawings, extension 24 protrudes from suction cup 12 and includes a tunnel 26 which runs from the end 28 of extension 24 to interior chamber 30 within suction cup 12. Vacuum from vacuum source 14 is conveyed by connector 22, and flexible tube 32 which includes a collapsible annular corrugation 38 and which extends from the back 34 of suction cup 12 to interior chamber 30.

When suction cup 12 is placed against a contact lens 36 which is positioned on the eye, and vacuum is supplied by vacuum source 14, air passes through tunnel 26 in extension 24 into interior chamber 30 of suction cup 12. The high velocity of the air passing through tunnel 26 and over the edge 37 of lens 36 creates a pressure differential (the Bernoulli principle) between the air at the stagnation point at the edge of the lens as opposed to the air above the lens. This causes the edge 37 of contact lens 36 to draw up into the tunnel 26, consequently blocking the tunnel. As a result, a pressure differential is created between the air above and the air below the lens 36 within suction cup 12. This causes the entire lens 36 to be sucked tightly against the suction cup rim 35.

Shown in FIGS. 2 and 3 of the drawings is collapsible annular corrugation 38 integrally formed in tube 32, which extends from the back 34 of suction cup 12. The configuration of this collapsible annular corrugation 38 has been designed to perform a special function hereinafter described. The corrugation has a shape which is, in its relaxed state, in rather like a slightly flattened doughnut in appearance, i.e., the corrugation has flattened upper and lower surfaces. These flattened upper and lower surfaces serve to increase the area of the corrugation 38 exposed to the greater atmospheric pressure which exists outside as compared to the air pressure inside when vacuum is applied to the suction cup 12. The pressure differential acts on the flattened surfaces of the corrugation 38 and causes them to collapse. If the corrugation were shaped, for instance, like a bulb, atmospheric pressure acting on the exterior would cause the bulb to shrink in diameter rather than to shrink in length, as does the instant invention. The corrugation is also thinner in cross-section than the rest of the suction cup 12 or flexible tube 32 which aids in the collapsing of the corrugation 38. In operation, when suction cup 12 is placed in contact with a contact lens 36 supported on an eye, and vacuum supplied by vacuum source 14 has caused the edge of the lens to seal off the tunnel 26, the collapsible annular corrugation 38 collapses into itself which withdraws cup 12 away from the eye. This drawing away of the contact lens 36 from the eye is effected by the sealing of the rim 35 of suction cup 12 to the lens 36, whereupon the vacuum within suction cup 12 causes the corrugation 38 to collapse into itself, as best seen in FIG. 3, thereby drawing the lens 36 away from the eye. The lens 36 is drawn away from the eye automatically and no movement of the user's hand is necessary or required. Collapsible annular corrugation 38 also is effective to reduce the force exerted by cup 12 against the eye during insertion or removal of a contact lens, by acting as a cushion and also a universal joint. Along these same lines, suction cup 12 and annular corrugation 38 may be constructed of a soft, flexible material, such as, for instance, silicone polymer, to cushion the force of the suction cup 12 against and to also aid in conforming to the shape of a contact lens.

As shown in FIG. 4 of the drawings, in an alternate embodiment of the invention, suction cup 40 has an extension 42 emanating from one side. Formed in extension 42 is a tunnel 44 with aperture 46 at its outermost point. Tunnel 44 is curved or spiralled, in order to increase the width of the lens edge under the tunnel, because the increased width of tunnel 44 provides a longer lens edge unrestrained from rising in the tunnel 44. Consequently, it is easier to lift the edge of the lens from the eye.

Figure 5:
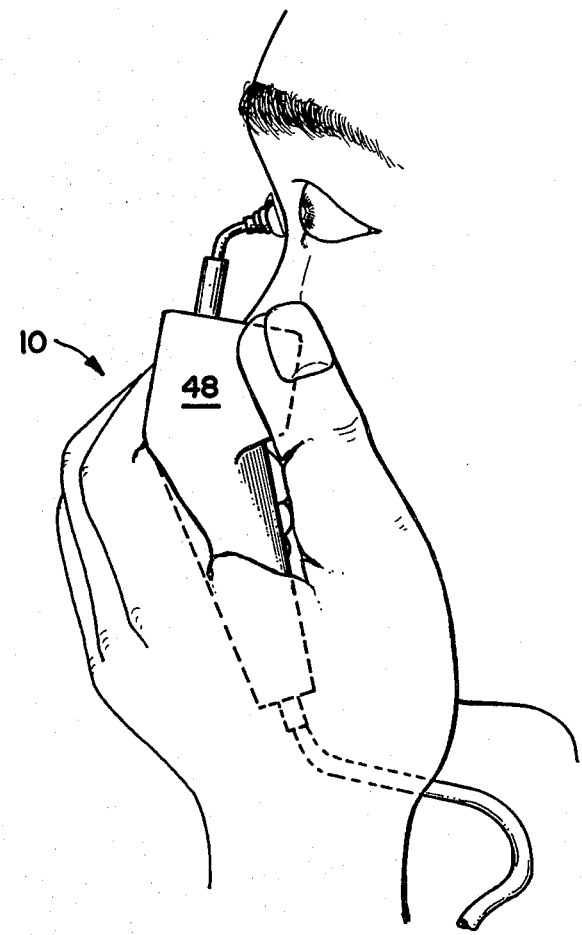
FIG. 5 of the drawings is a side view showing one embodiment of an improved contact lens insertion and removal device showing, in particular, a cheek support.

As shown in FIG. 5 of the drawings, improved lens insertion device 10 includes cheek support 48 which is placed against the cheekbone of the user to help align suction cup 10 with the eye.

The foregoing description and drawings merely explain and illustrate the invention and the invention is not limited thereto, except insofar as the appended claims are so limited as those skilled in the art who have the disclosure before them will be able to make modifications and variations therein without departing from the scope of the invention.

It is claimed:

1. A device for inserting into and removing from an eye a soft contact lens comprising:
   a suction cup having an extension projecting outwardly therefrom for engaging a soft contact lens, said extension being of a length sufficient to extend to at least the edge of said contact lens when said cup is engaged with said lens and having a passage formed therein for communicating air remote from said contact lens to a chamber formed between said suction cup and said contact lens;
   vacuum means connected to said suction cup for applying a vacuum to the chamber formed between said suction cup and said soft contact lens; and
   a collapsible member intermediate said suction cup and said vacuum means having openings therein communicating said suction cup and said vacuum means, said collapsible member being generally annular in shape and having flattened upper and lower surfaces, said flattened surfaces being dimensioned so that the surface area of the collapsible member is large enough that the atmospheric pressure is greater on the exterior of the flattened surfaces than the pressure acting on the interior surface when vacuum is applied to collapse said collapsible member whereby said suction cup and the contact lens contained thereon are caused to be automatically withdrawn from the eye without movement of the user's hand.

2. The invention according to claim 1 wherein said device includes tubular handle means interposed between said suction cup and said vacuum means for conveying vacuum from said vacuum means to said suction cup.

3. The invention according to claim 2 wherein connector means are disposed between said tubular handle means and said suction cup to position said tubular handle means as closely as possible to the user's hand and to angle said suction cup in relation to said tubular handle means thereby maximizing accuracy in inserting and removing a lens from an eye.

4. The invention according to claim 2 wherein said tubular handle means includes cheek support means for engaging the user's cheek and supporting said device while inserting and removing a contact lens from the human eye, said cheek support means further facilitating positioning of said suction cup onto said contact lens.

5. The invention according to claim 4 wherein said tubular handle means is curved proximate to said suction cup to permit gripping of the device as closely as possible to the eye to provide the greatest degree of accuracy in placement of said suction cup on the lens.

6. A device for inserting into and removing from an eye a soft contact lens comprising:
   a suction cup having an extension projecting outwardly therefrom for engaging a soft contact lens, said extension being adapted to extend to the edge of the contact lens and having a spiralled passage formed therein for communicating air from outside a soft contact lens to a chamber formed between said suction cup and the soft contact lens; and
   vacuum means for applying a vacuum to the chamber between said suction cup and the soft contact lens whereby when a vacuum is applied therebetween the edge of the lens is initially lifted from the eye breaking the surface tension between the lens and the eye enabling the lens to be removed thereafter from the eye.

7. The device as described in claim 6 further comprising a collapsible member intermediate said suction cup and said vacuum means having openings therein communicating said suction cup and said vacuum means, said collapsible member being generally annular in shape and having flattened upper and lower surfaces, said flattened surfaces being dimensioned so that the surface area of the collapsible member is large enough that the atmospheric pressure is greater on the exterior of the flattened surfaces than the pressure acting on the interior surface when vacuum is applied to collapse said collapsible member whereby said suction cup and the contact lens contained thereon are caused to be automatically withdrawn from the eye without movement of the user's hand.

* * * * *